United States Patent [19]

Immer et al.

[11] 4,118,380
[45] Oct. 3, 1978

[54] DECAPEPTIDE ANALOGS OF SOMATOSTATIN

[75] Inventors: Hans U. Immer, Mount Royal; Nedumparambil A. Abraham, Dollard des Ormeaux, both of Canada

[73] Assignee: Ayerst, McKenna & Harrison Limited, Montreal, Canada

[21] Appl. No.: 818,500

[22] Filed: Jul. 25, 1977

[51] Int. Cl.² .................................... C07C 103/52
[52] U.S. Cl. .................................... 260/112.5 S
[58] Field of Search .......................... 260/112.5 S

[56] References Cited

U.S. PATENT DOCUMENTS 4,020,157  7/1975  Abraham et al. ............. 260/112.5 S

FOREIGN PATENT DOCUMENTS 827,530  10/1975  Belgium ........................ 260/112.5 S
2,460,469  12/1974  Fed. Rep. of Germany .... 260/112.5 S
7,602,395  9/1976  Netherlands .................. 260/112.5 S

*Primary Examiner*—Delbert R. Phillips
*Attorney, Agent, or Firm*—Stephen Venetianer

[57] ABSTRACT

Compounds of the formula 1 or 1a

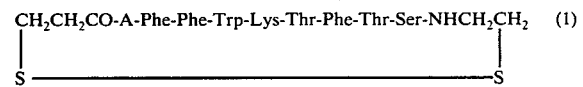

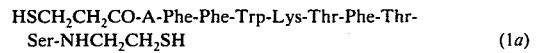

in which A is Gly-Asn or Lys-Gly, or therapeutically acceptable salts thereof are disclosed. The compounds of formulae 1 and 1a are useful for the management of diabetes and the treatment of acromegaly in mammals. Compositions and methods for their use also are disclosed.

10 Claims, No Drawings

DECAPEPTIDE ANALOGS OF SOMATOSTATIN

BACKGROUND OF THE INVENTION a. Field of Invention

This invention relates to derivatives of the tetradecapeptide somatostatin. More particularly, this invention concerns decapeptide derivatives in which $Lys^4$ or $Asn^5$ is replaced with a residue of glycine, salts thereof, a process for preparing said derivatives and salts, intermediates used in the process and methods for using the decapeptide derivatives and their salts.

b. Prior Art

The name "somatostatin" has been proposed for the factor found in hypothalamic extracts which inhibits the secretion of growth hormone (somatotropin). The structure of this factor has been elucidated by P. Brazeau et al., Science, 179, 77(1973) and reported to have the following tetradecapeptide structure:

$$\text{H—Ala—Gly—Cys—Lys—Asn—Phe—Phe—Trp—Lys—Thr—Phe—Thr—Ser—Cys—OH}$$
(with disulfide bridge between the two Cys)

The constitution of the tetradecapeptide somatostatin has been confirmed by synthesis; for example, see D. Sarantakis and W. A. McKinley, Biochem. Biophys. Res. Comm., 54, 234(1973), J. Rivier et al., Compt. Rend. Ser. D, 276, 2737(1973) and H. U. Immer et al., Helv. Chim. Acta, 57, 730(1974).

The important physiological activity of this tetradecapeptide established it as a compound of significance for clinical pharmacology relating to the treatment of acromegaly and the management of diabetes; for example, see K. Lundbaek et al., Lancet, 2, 131(1970) and R. Guillemin in "Chemistry and Biology of Peptides", J. Meienhofer, Ed., 3rd American Peptide Symposium Boston 1972, Ann Arbor Science Publications, Ann Arbor, Mich., 1972.

Since the structure and physiological activity of somatostatin was determined, a number of analogs of somatostatin have been reported, for instance see the report by J. Rivier et al., in "Peptides 1976", Editions de l'Universite de Bruxelles, Brussels, Belgium, edited by A. Loffet, 1977, 99. 427–451. More specifically, a number of shortened derivatives of somatostatin have been reported, for example: Netherlands patent application Ser. No. 7,602,395 published Sept. 14, 1976, discloses compounds of the formula $$\text{CH}_2\text{CH}_2\text{CO—X—Y—Phe—Phe—Trp—Lys—Thr—Phe—Thr—Ser—NHCH}_2\text{CH}_2$$
(with S—S bridge)

in which X is Lys, Nle or Cys and Y is Asn, Gln or Thr; Belgium Pat. No. 827,530 issued Oct. 3, 1975, discloses compounds of the formula $$\text{CH}_2\text{CH}_2\text{CO—W—V—Phe—Phe—Trp—W—Thr—Phe—Thr—Ser—NHCH}_2\text{CH}_2$$
(with S—S bridge)

in which V is Asn or Ala and W is Lys or Orn; and by H. U. Immer et al., in U.S. Pat. No. 4,020,157, issued Apr. 26, 1977, discloses compounds of the formula $$\text{CH}_2\text{CH(R)CO—Lys—Asn—Phe—Phe—Trp—Lys—Thr—Phe—Thr—Ser—NHCH}_2\text{CH}_2$$
(with S—S bridge)

in which R is hydrogen or $NHR^1$ wherein $R^1$ is lower aliphatic acyl or benzoyl.

The present invention discloses novel decapeptide derivatives of somatostatin in which $Lys^4$ or $Asn^5$ is replaced by a residue of glycine. Thus, these derivatives differ from the reported derivatives of somatostatin by having a different arrangement of amino acids. The derivatives of this invention possess a physiological activity similar to that of somatostatin. The derivatives are prepared readily by a convenient process, which includes the following advantages: the process starts from readily available materials, avoids noxious reagents, is executed facilely and utilizes easily removable protecting groups.

The foregoing advantages and attributes render the peptides of this invention useful for the management of diabetes and for the treatment of acromegaly.

SUMMARY OF THE INVENTION

The peptides of this invention are represented by formulae 1 and 1a; formula 1 representing the cyclic peptides of this invention and formula 1a representing the linear reduced form $$\text{CH}_2\text{CH}_2\text{CO-A-Phe-Phe-Trp-Lys-Thr-Phe-Thr-Ser-NHCH}_2\text{CH}_2 \quad (1)$$
(with S—S bridge)

$$\text{HSCH}_2\text{CH}_2\text{CO-A-Phe-Phe-Trp-Lys-Thr-Phe-Thr-Ser-NHCH}_2\text{CH}_2\text{SH} \quad (1a)$$

in which A is Gly-Asn or Lys-Gly.

The therapeutically acceptable salts of the compounds of formulae 1 and 1a are also included within the scope of this invention.

The peptides of this invention are prepared by a process which comprises: reacting according to the azide coupling method a first peptide hydrazide of the formula 2

$$\text{Trt-SCH}_2\text{CH}_2\text{CO-A}^1\text{-Phe-Phe-NHNH}_2 \quad (2)$$

in which $A^1$ is Gly-Asn or Lys(Boc)-Gly with a second peptide of the formula 3

H-Trp-Lys(Boc)-Thr(Bu$^t$)-Phe-Thr(Bu$^t$)-Ser(Bu$^t$)-
NHCH$_2$CH$_2$S-Trt  (3)

to obtain the linear peptide of formula 4

Trt-SCH$_2$CH$_2$CO-A$^1$-Phe-Phe-Trp-Lys(Boc)-
Thr(Bu$^t$)-Phe-Thr(Bu$^t$)-Ser(Bu$^t$)-NHCH$_2$CH$_2$-
Trt  (4)

in which A$^1$ is as defined herein; followed by oxidizing said linear peptide with iodine or thiocyanogen to obtain the corresponding cyclic disulfide derivative of formula 5

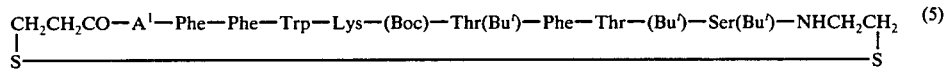

in which A$^1$ is as defined herein and subsequently removing all remaining protecting groups under moderately acidic conditions to obtain the corresponding peptide of formula 1; or followed by subjecting said linear peptide to treatment with either mercuric acetate, mercuric chloride, silver acetate or silver nitrate to remove selectively the sulfhydryl protecting groups to obtain the mercuric or disilver salt, respectively, of the corresponding disulfhydryl derivative; converting the latter salt to its corresponding free disulfhydryl derivative by treatment with hydrogen sulfide, oxidizing said last-named derivative by treatment with oxygen, 1,2-diiodoethane, sodium or potassium ferricyanide or iodine to obtain the corresponding cyclic disulfide derivative and removing the remaining protecting groups under moderately acid conditions to obtain the desired peptide of formula 1. Alternatively, said cyclic disulfide derivative is reduced to said corresponding free disulfhydryl derivative by agents known to be effective for reducing known cyclic disulfides to their corresponding disulfhydryl derivatives.

A further aspect of this invention comprises the removal of all the protecting groups from the aforementioned linear peptide of formula 4 or the aforementioned disulfhydryl derivatives under moderately acidic conditions to obtain the linear reduced form of the peptide of this invention of formula 1a, HSCH$_2$CH$_2$CO-A-Phe-Phe-Trp-Lys-Thr-Phe-Thr-
Ser-NHCH$_2$CH$_2$SH  (1a)

in which A is as defined herein.

The latter compound is also obtained by direct reduction of the cyclic peptide of formula 1 by agents known to be effective for reducing known cyclic disulfides to their corresponding disulfhydryl derivatives. If desired said reduced form of the cyclic peptide is converted to the corresponding derivative of formula 1 by one of the above oxidizing agents.

DETAILS OF THE INVENTION

In general the abbreviations used herein for designating the amino acids and the protective groups are based on recommendations of the IUPACIBU Commission on Biochemical Nomenclature, see Biochemistry, 11, 1726–1732(1972). For instance, Ala, Gly, Cys, Lys, Asn, Asp, Phe, Trp, Thr and Ser represent the "residues" of L-alanine, glycine, L-cysteine, L-lysine, L-asparagine, L-aspartic acid, L-phenylalanine, L-tryptophan, L-threonine and L-serine, respectively. The term "residue" refers to a radical derived from the corresponding α-amino acid by eliminating the hydroxyl of the carboxy group and one hydrogen of the α-amino group.

A number of procedures or techniques for the preparation of peptides have hitherto been well established and found in general textbooks of peptide chemistry; for example K. D. Kopple, "Peptides and Amino Acids", W. A. Benjamin, Inc., New York, 1966, pp. 33–51 and E. Schröder and K. L. Lübke, "The Peptides"; Vol. I; Academic Press, New York, 1965, pp. 3–128. For instance, the functional groups which are not involved in the peptide bond formation reaction are protected by a protecting group or groups prior to the condensation reaction. Examples of protecting groups for an amino group not involved in the peptide bond formation are: the urethane type which include benzyloxycarbonyl (represented by Z), t-butoxycarbonyl (represented by Boc), α,α-dimethyl-3,5-dimethoxy-benzyloxycarbonyl(represented by Ddz), 2-(p-biphenyl)-isopropyloxycarbonyl (represented by Bpoc), p-chlorobenzyloxycarbonyl, p-methoxybenzyloxycarbonyl, p-nitrobenzyloxycarbonyl, isonicotinyloxycarbonyl, isobornyloxycarbonyl, isopropyloxycarbonyl, or ethoxycarbonyl; the acyl type protecting groups which include formyl, trifluoroacetyl, phthalyl, acetyl (Ac), nitrophenylsulfenyl, or toluenesulfonyl; the alkyl type protecting groups which include triphenylmethyl (or trityl, represented by Trt), trimethylsilyl or benzyl; the preferred protecting groups in the process of this invention are benzyloxycarbonyl, t-butoxycarbonyl, triphenylmethyl and α,α-dimethyl-3,5-dimethoxy-benzyloxycarbonyl.

The hydroxyl of serine and threonine can be optionally protected by acetyl, tosyl, benzoyl, tert-butyl (represented by Bu$^t$) and benzyl; the preferred protecting group is tert-butyl. The carboxylic acid function of a peptide or amino acid can be considered protected by a lower alkyl or lower aralkyl ester which include methyl (represented by OMe), ethyl (represented by OEt), t-butyl (represented by OBu$^t$), or benzyl (represented by OBzl) esters; and also by substituted hydrazides which include t-butoxycarbonyl hydrazide (represented by NHNH-Boc), benzyloxycarbonyl hydrazide (represented by NHNH-Z), or α,α-dimethyl-3,5-dimethoxy-benzyloxycarbonyl hydrazide (represented by NHNH-Ddz). A peptide or amino acid is coupled with another peptide or amino acid to form a new peptide by the elimination of water (i.e. dehydrative coupling). More specifically, the hydroxyl portion of a free carboxy group in a peptide or amino acid and a hydrogen atom in a free amino group of the other peptide or amino acid are eliminated to form a new amide bond joining the peptide or amino acid starting materials. To promote facile condensation of a peptide free carboxy group with a free amino group of another peptide to form a new peptide bond, the free carboxy group must be activated. Descriptions of such carboxy activating groups are included in the general textbooks of peptide chemistry by Kopple, or Schroder and Lubke, cited above. Examples of carboxy group activating agents for a carboxylic acid are thionyl chloride, thionyl bromide, methyl chloroformate, a dialkylcarbodiimide (e.g., dicyclohexylcarbodiimide); N-hydroxysuccinimide, 2,4,5-trichlorophenol, pentachlorophenol, p-nitrophenol or 1-hydroxybenzotriazole in the presence of a dialkylcarbodiimide; and in the case of a hydrazide the carboxylic group activating agent is nitrous acid. Examples of the activated form of the terminal carboxy group are acid chloride, anhydride, azide, activated ester, or 0-acyl urea of a dialkylcarbodiimide. The following activated esters have proved to be particularly suitable in the process of this invention: 2,4,5-trichlorophenyl (represented by OTcp), pentachlorophenyl (represented by OPcp), p-nitrophenyl (represented by ONp), or 1-benzotriazolyl; the succinimido group is also useful for such activation.

The coupling of a peptide or amino acid having the activated carboxy with the peptide or amino acid having a free amino group is conducted in an inert organic solvent at a temperature from $-30°$ C. to about $50°$ C. For coupling to occur, the amino group must not be protonated. A sufficient amount of an organic proton acceptor is added to the above reaction mixture until the amino group is no longer protonated (usually pH 7.0 to 8.0).

The term "azide coupling method" as used herein refers to the method of activating the terminal carboxy of a peptide fragment with an axide and condensing the latter peptide azide with another peptide having a free amino group. The peptide azide is conveniently prepared by reacting a peptide hydrazide with a reagent which furnishes nitrous acid in situ. Suitable reagents for this purpose include organic nitrites (e.g. t-butyl nitrite and isoamyl nitrite) or alkali metal nitrite salts (e.g. sodium nitrite and potassium nitrite) in the presence of a mineral acid such as hydrogen chloride or sulfuric or phosphoric acid. The corresponding peptide azide thus obtained is then reacted with a peptide or compound having a free amino group to obtain the desired peptide. Preferred conditions for the azide method of coupling comprise reacting the peptide hydrazide with nitrous acid, generated in situ from an organic nitrite in the presence of a strong acid, preferably hydrogen chloride, (pH ranging usually from 0.1 to 2), in an anhydrous inert organic solvent, for example, dimethylformamide, dimethyl sulfoxide, ethyl acetate, methylene dichloride, tetrahydrofuran, dioxane, and the like at $-30°$ to $20°$ C., preferably at about $-15°$ C. for 10 to 30 minutes to obtain the corresponding azide. The peptide azide can be isolated and crystallized but is preferably allowed to remain in the reaction mixture. Thereafter the azide in the above mixture is reacted with the peptide unit or compound having the free amino group at temperatures ranging from $-30°$ to $20°$ C. for about 1 to 2 hours and then at $0°$ to $30°$ C. for 10 to 30 hours. An acid acceptor, preferably an organic proton acceptor, for example N-ethyldiisopropylamine, N-ethylmorpholine or triethylamine, is present in the reaction mixture in order to make the reaction medium slightly alkaline, preferably pH 7.0 to 9.0. See also the above cited textbooks of Kopple or Schröder and Lübke for additional descriptions of this method.

The terms peptide, polypeptide, tripeptide, hexapeptide, and the like as used herein are not limited to refer to the respective parent peptides but are also used with reference to modified peptides with or without functionalized or protecting groups. The term "peptide" as used herein is used with reference to a peptide with two to ten amino acid residues.

The abbreviation Me represents a methyl group, $NHNH_2$ represents a hydrazide group and $N_3$ represents an azide group.

The term "lower alkyl" as used herein contemplates hydrocarbon radicals having one to three carbon atoms and includes methyl, ethyl and propyl.

The term "lower alkanol" as used herein means monohydric alcohols having one to four carbon atoms in a straight or branched chain and includes methanol, ethanol, isopropanol and butanol.

The term "mineral acid" as used herein contemplates the strong inorganic acids and includes hydrochloric, hydrobromic, sulfuric, or phosphoric acid. When the term is used in conjunction with an anhydrous system, anhydrous hydrogen chloride is the preferred mineral acid.

The term "mildly acidic conditions" as used herein contemplates conditions in which an aqueous solution of an organic acid, for example 30–80% aqueous formic, acetic or propionic acid, preferably 70–80%, or mixtures thereof, is a principal component of the reaction medium.

The term "moderately acidic conditions" as used herein contemplates conditions in which concentrated organic acids or solutions of the mineral acids are used as a principal component of the reaction medium at temperatures ranging from about $-30°$ to $30°$ C. Examples of preferred conditions in this case include the use of 50 to 100% trifluoroacetic acid at $0°$ to $30°$ C., or 0.1–12N hydrochloric acid in aqueous solution or in solution in an organic solvent, or hydrogen chloride in solution in anhydrous organic solvents at $-20°$ to $10°$ C.

The term "organic nitrite" includes the commercially available alkyl nitrites, for instance, t-butyl nitrite, isoamyl nitrite, and the like.

The term "organic proton acceptor" as used here includes triethylamine, N-ethylmorpholine, N-ethyldiisopropylamine and the like.

The peptides of this invention are obtained in the form of the free base or as an acid addition salt directly from the process of this invention. The peptides in the form of the free bases are readily obtained from the corresponding acid addition salt by conventional methods, for example a solution of the acid addition salt is passed through an anionic exchange resin ($OH^-$form) to obtain the free base. The free base is also obtained from the acetic acid addition salt by repeated lyophilization of the latter salt from aqueous solution. The acetic acid adition salt is readily obtained from another acid addition salt by treatment with the appropriate ion exchange resin in the manner hereinafter disclosed. The peptides of this invention are obtained in the form of a therapeutically acceptable acid addition salt either directly from the process of this invention or by reacting the peptide with one or more equivalents of the appropriate acid. Examples of preferred non toxic salts are those with therapeutically acceptable organic acids, e.g. acetic, lactic, succinic, benzoic, salicyclic, methanesulfonic, toluenesulfonic, or pamoic acid, as well as polymeric acids such as tannic acid or carboxymethyl cellulose, and salts with inorganic acids such as the hydrohalic acids, e.g. hydrochloric acid, or sulfuric acid, or phosphoric acid. If desired a particular acid addition salt is converted into another acid addition salt, e.g., a salt with a non toxic, pharmaceutically acceptable acid, by treatment with the appropriate ion exchange resin in the manner described by R. A. Boissonas, et al., Helv.

Chim. Acta, 43, 1349 (1960). Suitable ion exchange resins are cellulose based cation exchangers, for example carboxymethylcellulose, or chemically modified, cross-linked dextrancation exchangers, for example, those of the Sephadex C type, and strongly basic anion exchange resins, for example those listed in J. P. Greenstein and M. Winitz "Chemistry of the Amino Acids", John Wiley and Sons, Inc., New York and London, 1961, Vol. 3, p. 1456.

The peptides of this invention give complex salts with heavy metal ions. An example of a pharmaceutically acceptable heavy metal complex is a complex formed with zinc or with zinc protamine.

The peptides produced by the process of this invention, as well as their corresponding therapeutically acceptable salts, are useful because they possess the pharmacological activity of the natural tetradecapeptide somatostatin. Their activity is demonstrated readily in pharmacological tests such as a modification [A. V. Schally et al., Biochem. Biophys. Res. Commun., 52, 1314 (1973) and J. Rivier et al., C.R. Acad. Sci. Paris, Ser. D, 276, 2737 (1973)] of the in vitro method of M. Saffran and A. V. Schally, Can. J. Biochem. Physiol., 33, 405 (1955).

The activity of the peptides of formula 1, or 1a, of this invention is demonstrated also in vivo in a modification of the pentobarbital-induced increase in plasma growth hormone level in the rat as described by Brazeau et al., cited above. In this test the peptides of this invention show a level of activity similar to that of somatostatin.

The peptides of formula 1, or 1a, or the salts thereof are useful for the treatment of acromegaly and related hypersecretory endocrine states and in the management of diabetes in mammals; see for example, P. Brazeau et al., cited above. When the peptides or salts thereof are employed for such treatment or management, they are administered systemically, preferably parenterally, in combination with a pharmaceutically acceptable liquid carrier. The peptides of formulae 1 and 1a have a low order of toxicity. The proportion of the peptide or salt thereof is determined by its solubility in the given carrier, by the given carrier, or by the chosen route of administration. When the peptide or a salt thereof is used in a sterile aqueous solution, such solution may also contain other solutes such as buffers or preservatives, as well as sufficient amounts of pharmaceutically acceptable salts or glucose to make the solution isotonic. The dosage will vary with the form of administration and with the particular species to be treated and is preferably kept at a level of from 1 meg to 300 meg per kilogram body weight. However, a dosage level in the range of from about 1 meg to about 50 meg per kilogram body weight is most desirably employed in order to achieve effective results.

The peptides or salts thereof may also be administered in one of the long-acting, slow-release or depot dosage forms described below, preferably by intramuscular injection or by implantation. Such dosage forms are designed to release from about 0.1 meg to about 50 meg per kilogram body weight per day.

It is often desirable to administer the agent continuously over prolonged periods of time in long-acting, slow-release or depot dosage forms. Such dosage forms may either contain a pharmaceutically acceptable salt of the peptide having a low degree of solubility in body fluids, for example one of those salts described below, or they may contain the peptide in the form of a water-soluble salt together with protective carrier which prevents rapid release. In the latter case, for example, the peptide may be formulated with a non-antigenic partially hydrolyzed gelatin in the form of a viscous liquid; or the peptide may be absorbed on a phramaceutically acceptable solid carrier, for example, zinc hydroxide, and may be administered in suspension in a pharmaceutically acceptable liquid vehicle; or the peptide may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton, Pa., 1970. Long-acting, slow-release preparations of the peptide produced according to the process of this invention may also be obtained by microencapsulation in a pharmaceutically acceptable coating, for example, gelatine, polyvinyl alcohol or ethyl cellulose. Further examples of coating materials and of the processes used for microencapsulation are described by J. A. Herbig in "Encyclopedia of Chemical Technology", Vol. 13, 2nd Ed., Wiley, New York 1967, pp. 436–456. Such formulations, as well as suspensions of salts of the peptide which are only sparingly soluble in body fluids, for example salts with pamoic acid or tannic acid, are designed to release fom about 1.0 mcg to about 100 mcg of the active compound per kilogram body weight per day, and are preferably administered by intramuscular injection. Alternatively, some of the solid dosage forms listed above, for example certain sparingly water-soluble salts or dispersions in or adsorbates on solid carriers of salts of the peptide, for example dispersions in a neutral hydrogel of a polymer of ethylene glycol methacrylate or similar monomers cross-linked as described in U.S. Pat. No. 3,551,556, may also be formulated in the form of pellets releasing about the same amounts as shown above and may be implanted subcutaneously or intramuscularly.

PROCESS

The first peptide hydrazide of formula 2

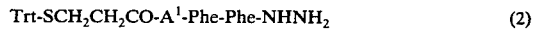

Trt-SCH$_2$CH$_2$CO-A$^1$-Phe-Phe-NHNH$_2$     (2)

in which A$^1$ is Gly-Asn or Lys(Boc)-Gly is prepared by dehydrative coupling of Trt-SCH$_2$CH$_2$COOH with a tetrapeptide of formula 6

H-A$^1$-Phe-Phe-OMe     (6)

in which A$^1$ is as defined herein to obtain the corresponding tetrapeptide of formula 7

Trt-SCH$_2$CH$_2$CO-A$^1$-Phe-Phe-OMe     (7)

followed by reacting the latter compound with hydrazine hydrate to obtain the corresponding compound of formula 2.

The tetrapeptides of formula 6 are conveniently prepared by the successive dehydrative coupling of amino acids.

The compound of formula 6 in which A$^1$ is Gly-Asn is prepared by coupling an activated ester of Boc-Gly- OH, preferably the trichlorophenyl ester, with H-Asn-Phe-Phe-OMe (described by H. U. Immer et al. in U.S. Pat. No. 3,917,578, issued Nov. 4, 1975) at 0° to 30° C. for 10 to 30 hours in an inert organic solvent, preferably dimethylformamide, to obtain Boc-Gly-Asn-Phe-Phe-OMe followed by removal of the protecting group, Boc, under moderately acidic conditions, preferably using trifluoroacetic acid at −10° to 10° C. for 30 to 180 minutes, to obtain the corresponding compound of formula 6 in which $A^1$ is Gly-Asn in the form of the salt with the acid used for deprotection. The free base of the latter compound can be obtained by conventional methods, i.e. ion exchange chromatography or neutralization with a suitable base, however, it is preferable to form the free base of the compound in situ during the next reaction of the compound. The latter consideration concerning the formation of a free base is also applicable to the other intermediates which are isolated as the acid addition salt.

The compound of formula 6 in which $A^1$ is Lys(Boc)-Gly is prepared in the following manner. Equimolar amounts of Z-Gly-OH and H-Phe-Phe-OMe (described in U.S. Pat. No. 3,917,578, noted above) are dehydratively coupled, preferably in the presence of 1.1 to 1.5 molar equivalents of dicyclohexylcarbodiimide and 1.5 to 3 molar equivalents of 1-hydroxybenzotriazole in an inert organic solvent, preferably dimethylformamide, at 0° to 30° C. for 10 to 30 hours, to obtain Z-Gly-Phe-Phe-OMe. The protecting group, Z, is removed by agitating a mixture of the latter compound and a noble metal hydrogenation catalyst, for example palladium on carbon, in an inert organic solvent, preferably methanol, ethanol or acetic acid, under an atmosphere of hydrogen. In this manner the tripeptide, H-Gly-Phe-Phe-OMe, is obtained. The latter compound and Z-Lys(Boc)-OH are dehydratively coupled, preferably by reacting substantially equimolar amounts of the tripeptide and an activated ester of Z-Lys(Boc)-OH, preferably the p-nitrophenyl ester, in an inert organic solvent, for example dimethylformamide, in the presence of a sufficient amount of an organic proton acceptor, preferably N-ethylmorpholine, to adjust the solution to pH 7.0 to 7.5 at 0° to 30° C. for 10 to 30 hours, to obtain Z-Lys(-Boc)-Gly-Phe-Phe-OMe. The protecting group, Z, is removed from the latter compound in the same manner as described above to obtain the compound of formula 6 in which $A^1$ is Lys(Boc)-Gly.

The compounds of formula 6 in which $A^1$ is a defined herein are dehydrative coupled with Trt-SCH$_2$CH$_2$COOH to obtain the corresponding compounds of formula 7 in which $A^1$ is as defined herein. One convenient method to achieve this coupling is to react substantially equimolar amounts of Trt-SCH$_2$CH$_2$-COOH and the compound of formula 6 in the presence of 1.1 to 1.5 molar equivalents of dicyclohexylcarbodiimide, 1.5 to 2.0 molar equivalents of 1-hydroxybenzotriazole and a sufficient amount of an organic proton acceptor, preferably N-ethylmorpholine, to adjust the solution of pH 7.0 to 7.5 in an inert organic solvent, preferably dimethylformamide, at 0° to 30° C. for one to three days. Another useful method of coupling is to react substantially equimolar amounts of the compound of formula 6 and an activated ester of Trt-SCH$_2$-CH$_2$COOH, preferably the pentachlorophenyl ester, in the presence of a sufficient quantity of an organic proton acceptor, preferably N-ethylmorpholine, to adjust the solution to pH 7.0 to 7.5 in an inert organic solvent, preferably, dimethylformamide, at 0° to 30° C. for 10 to 30 hours to obtain the corresponding compounding compound of formula 7.

The compound of formula 7 is dissolved in an inert organic solvent, for example methanol, ethanol, dimethylformamide, and the like, preferably methanol. The solution is treated with an excess of hydrazine hydrate, for example 15 to 30 molar equivalents. The reaction mixture is kept at about 0° to 30° C. for about 10 to 30 hours to obtain the corresponding compound of formula 2 in which $A^1$ is as defined herein.

In the next step of the process of this invention the aforementioned first peptide hydrazide of formula 2 and the second peptide of formula 3 H-Trp-Lys(Boc)-Thr(Bu$^t$)-Phe-Thr(Bu$^t$)-Ser(Bu$^t$)-NHCH$_2$CH$_2$S-Trt (described by H. U. Immer et al., in U.S. Pat. No. 3,917,581, issued Nov. 4, 1975) are coupled according to the azide coupling method to obtain the corresponding linear peptide of formula 4, Trt-SCH$_2$CH$_2$CO-A$^1$-Phe-Phe-Trp-Lys(Boc)-
   Thr(Bu$^t$)-Phe-Thr(Bu$^t$)-Ser(Bu$^t$)-NHCH$_2$CH$_2$S-
   Trt    (4)

in which $A^1$ is as defined herein.

A convenient and efficacious procedure for this step comprises dissolving the first peptide hydrazide 2 in which $A^1$ is as defined herein in an organic solvent, preferably dimethylformamide and cooling the mixture to about −20° to −10° C. A solution of about two to five molar equivalents of a strong acid in an inert organic solvent, preferably three molar equivalents of hydrogen chloride in ethyl acetate, is added to the above solution, followed by 1.0 to 1.5 molar equivalents of an organic nitrite, for example, 1.2 molar equivalents of t-butyl nitrite. In this manner the corresponding pentapeptide azide of formula Trt-SCH$_2$CH$_2$CO-A$^1$-Phe-Phe-N$_3$ in which $A^1$ is as defined herein is obtained. After about 10 to 20 minutes at about −20° to 0° C., a solution of substantially one molar equivalent of the compound of formula 3 and an organic proton acceptor in an inert organic solvent, preferably two to four molar equivalents of N-ethyldiisopropylamine in dimethylformamide, cooled to about −20° to 0° C., is added to the above solution containing said azide. The reaction mixture is then stirred at about −20° to 0° C. for 1 to 2 hours and then at about 20° to 30° C. for 20 to 30 hours. The solvent is evaporated under reduced pressure. The residue is triturated with cold water and methanol, and separation of the solid gives the aforementioned linear decapeptide of formula 4 in which $A^1$ is as defined herein.

The conversion of the proceding linear decapeptide of formula 4, obtained as described above, in which $A^1$ is as defined to the corresponding compound of formula 1 in which A is as defined herein as accomplished conveniently and efficiently by first subjecting the linear decapeptide to the action of iodine, preferably in the presence of a lower alkanol and/or acetic acid, whereby removal of the sulfhydryl protecting groups, i.e. Trt, and concomitant formation of the disulfide bridge occurs to give the corresponding cyclic disulfide derivative of formula 5.

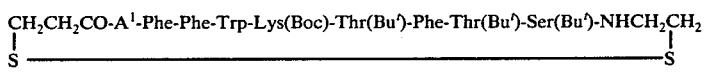

(5)

in which $A^1$ is as defined herein. Subsequent treatment of the latter compound under moderately acidic conditions removes the remaining protecting groups (i.e. Boc and Bu$^t$) to give the corresponding cyclic peptide of formula 1 in which A is as defined herein.

In a preferred embodiment of the above transformation the linear peptide of formula 4 is dissolved in acetic acid or methanol, ethanol or other suitable lower alkanol, for example, propanol, isopropanol or butanol. This solution is added to an excess of iodine (5 to 25, preferably 10 molar equivalents) dissolved in a lower alkanol, preferably 2–5% iodine in methanol). The time and temperature of this reaction is not critical; however, it is desirable to keep the reaction between 0° and 30° C. by regulating the addition to the iodine solution or by cooling of the reaction mixture, or by a combination of both. Under these conditions the addition usually takes 30 to 60 minutes. After the addition of iodine the mixture is stirred at 20° to 30° C. for 30 to 120 minutes, preferably for 60 minutes. Thereafter the mixture is cooled to about 0° C. and an excess of a mild reducing agent, preferably sodium thiosulfate in aqueous solution, is added in order to destroy excess iodine. The mixture is concentrated and the residue is suspended in water. Collection of the solid material affords the desired corresponding cyclic disulfide derivative of formula 5 in which $A^1$ is as defined herein.

Alternatively, the linear decapeptide 4 is converted to the aforementioned corresponding cyclic disulfide 5 derivative by the method of R. G. Hiskey and R. L. Smith, J. Amer. Chem. Soc., 90, 2677 (1968) using thiocyanogen.

Again alternatively, the above cyclic disulfide derivative 5 is also obtained by selectively removing the sulfhydryl protecting groups of the above linear peptide 4 by the action of a mercuric or silver salt, for example, mercuric acetate, mercuric chloride, silver acetate or silver nitrate, in an inert organic solvent, for example dimethylformamide or acetic acid, according to known methods; for example, see B. Kamber, and W. Rittel, Helv. Chem. Soc. 87, 4922 (1965) and R. G. Denkewalter et al., J. Amer. Chem. Soc., 91,502 (1969). The corresponding mercuric or disilver salt is then converted by hydrogen sulfide treatment to the corresponding free disulfhydryl derivative, see L. Zervas et al., cited above. The latter derivative is then converted to the aforementioned cyclic disulfide derivative by treatment with a mild oxidizing agent, for example iodine according to the method described hereinbefore, or oxygen according to the method of J. Rivier et al., C. R. Acad. Sci. Ser. D, 276,2737 (1973), or 1,2-diiodoethane according to the method of F. Weygand and G. Zumach, Z. Naturforsch. 17b, 807 (1962), or sodium or potassium ferricyanide according to the method of D. Jarvis et al., J. Amer. Chem. Soc., 83,4780 (1961).

Finally, the aforementioned cyclic disulfide derivative of formula 5 in which $A^1$ is as defined herein, is transformed into the cyclic decapeptide of formula 1 in which A is as defined herein by subjecting the former to moderately acidic conditions whereby the remaining protecting groups of the cyclic disulfide derivative are removed. Generally this step is carried out by dissolving the cyclic disulfide derivative in an reaction medium containing a strong acid at −10° to 20° C. for 10 to about 60 minutes. Examples of such media are 80 to 100% trifluoroacetic acid, 10 to 20% aqueous sulfuric acid, 10% phosphoric acid, 10–30% hydrobromic acid or 10 to 36% hydrochloric acid. An extremely useful medium is concentrated hydrochloric acid. Preferred conditions for this step include dissolving the cyclic disulfide in a minimum of concentrated hydrochloric acid cooled to −5° to 5° C. and stirring the mixture at −5° to 5° C. for 5 to 10 minutes under a nitrogen atmoshphere. Thereafter glacial acetic acid (10 vols.) is added, the solution is cooled to about −70° C. and lyophilized to give the corresponding cyclic decapeptide of formula 1 in which A is as defined herein. The latter product is purified further by ion exchange chromatography, preferably using a carboxymethyl cellulose cation exchanger and ammonium acetate as the eluant. In this case the peptide is obtained in the form of its acid addition salt with acetic acid. Alternatively, the peptide is purified by partition chromatography on a chemically modified cross-linked dextran; for example, Sephadex LH-20 or Sephadex G-25. In the case where Sephadex LH-20 is employed and methanol as the eluting solvent, the peptide is obtained in the form of its acid addition salt with hydrochloric acid. In the case where Sephadex G-25 and acetic acid or acetic acid-water-butanol is employed, the peptide is obtained in the form of its acetic acid addition salt. The latter salt, when subjected to repeated lyophilization from water yields the cyclic decapeptide of formula 1 in which A is as defined herein in the form of the free base.

The linear reduced form of the cyclic decapeptide of formula 1a in which A is as defined herein is obtained preferentially by removal of the protecting groups from the aforementioned linear decapetide of formula 4 in which $A^1$ is as defined. Convenient conditions for this deprotection step comprise dissolving the linear peptide 4 in concentrated hydrochloric acid at about 0° to 5° C. in an inert atmosphere, for example, nitrogen or argon. The mixture is kept at this temperature for 5 to 10 minutes. Subsequent isolation of the linear reduced form (1a, in which A is as defined herein) is accomplished in the same manner as described previously for the isolation of the cyclic undecapeptide of formula (1).

Also, the linear reduced form is obtained directly by reduction of the cyclic decapeptide of formula 1. Reduction with dithiothreitol according to the method of W. W. Cleland, Biochem. 3, 480 (1964) is preferred, although other agents known to be effective for the reduction of cyclic disulfides to the corresponding disulfhydryl derivative are applicable, for example, sodium bisulfite followed by hydrolysis of the intermediate dithiosulfate derivative.

The following examples illustrate further this invention.

EXAMPLE 1

Benzyloxycarbonyl-glycyl-phenylalanyl-phenylalanine Methyl Ester (Z-Gly-Phe-Phe-OMe)

To a stirred, cooled (0° C.) solution of benzyloxycarbonylglycine (955mg, 4.5 mmole) and 1-hydroxybenzotriazole (1.2 g, 9 mmole) in dimethylformamide (15 ml)

is added dicyclohexylcarbodiimide (1.03 g, 5 mmole). The mixture is stirred for 1 hour at 0° C. A cooled solution of phenylalanyl-phenylalanine methyl ester trifluoroacetate (2.0 g, 4.5 mmoles, described in U.S. Pat. No. 3,917,578, noted above) in dimethylformamide (20 ml) and N-ethyl morpholine (0.58 ml) is added and the mixture is stirred overnight at room temperature. The mixture is filtered and the filtrate is evaporated. The residue is dissolved in ethyl acetate (100 ml) and the solution is filtered. The filtrate is washed with 10% aqueous citric acid solution, saturated sodium chloride solution, saturated sodium bicarbonate solution and saturated sodium chloride solution. The solution is dried over magnesium sulfate (anhydrous) and evaporated. The residue is crystalized from ethyl acetate-petroleum ether (30°–60°) to give the title compound as crystals, mp 122°–124° C.

EXAMPLE 2

Benzyloxycarbonyl-($N^6$-t-butoxycarbonyl)lysyl-glycyl-phenylalanyl-phenylalanine Methyl Ester (Z-Lys(-Boc)-Gly-Phe-Phe-OMe)

A mixture of benzyloxycarbonyl-glycyl-phenylalanyl-phenylalanine methyl ester (1.5 g, 2.9 mmoles described in Example 1) and 5% palladium on carbon (0.15 g) in acetic acid 140 ml) is rapidly stirred under an atmosphere of hydrogen until the benzyloxycarbonyl group is removed. The mixture is filtered and the filtrate is evaporated. The residue is triturated with ether to give a precipitate of glycyl-phenylalanyl-phenylalanine methyl ester. A solution of benzyloxycarbonly-($N^6$-t-butoxycarbonyl)-lysine p-nitrophenyl ester [1.36 g, 2.7 mmoles, described by E. Sandrin and R. A. Boissonas, Helv. Chem. Acta. 46, 1637 (1963)] in dimethylformamide (20 ml) is added dropwise to a cooled solution of the above compound (1.2 g, 217 mmoles) and N-ethylmorpholine (1.35 ml, 2.7 mmoles). The reaction mixture is stirred overnight at room temperature and evaporated. The residue is dissolved in methanol (4 ml) and diethyl ether is added. The precipitate is crystallized from ethyl acetate-petroleum ether (30°–60° C.) to obtain the title compound, mp 139°–142° C.

EXAMPLE 3

3-Tritylthiopropionyl-($N^6$-t-butoxycarbonyl)lysyl-glycyl-phenylalanyl-phenylalanine Methyl Ester (7; Trt-SCH$_2$CH$_2$CO-Lys(Boc)-Gly-Phe-Phe-OMe)

A mixture of benzyloxycarbonyl-($N^6$-t-butyloxycarbonyl)lysyl-glycyl-phenylalanyl-phenylalanine methyl ester (1.4 g, 1.87 mmole, described in Example 2) and 5% palladium an carbon (0.14 g) in acetic acid (40 ml) is rapidly stirred under an atmosphere of hydrogen until the benzyloxycarbonyl group is removed. The mixture is filtered and the filtrate is evaporated. The residue is triturated with diethyl ether to give a precipitate of ($N^6$-t-butoxycarbonyl)lysyl-glycyl-phenylalanyl-phenylalanine methyl ester. 3-Tritylthiopropionic acid (508 mg, 1.46 mmole) is dissolved in dimethylformamide (10 ml) and 1-hydroxybenzotriazole (395 mg, 2.92 mmoles) is added. The mixture is cooled to 0° C. and a solution of dicyclohexylcarbodiimide (330 mg, 1.6 mmole) in dimethylformamide (10 ml) is added dropwise. The mixture is stirred for 1 hour at 0° C. and a solution of the above compound (980 mg, 1.46 mmole) in dimethylformamide (20 ml), containing N-ethylmorpholine (0.2 ml, 1.56 mmole) is added. The reaction mixture is stirred at room temperature for 2 days and evaporated. The residue is dissolved in ethyl acetate and the mixture is filtered. The filtrate is washed successively with cold citric acid solution (1N), water, sodium bicarbonate solution (saturated), water and sodium chloride solution, dried over sodium sulfate and evaporated. The residue is dissolved in hot ethyl acetate and the solution is cooled to give a precipitate. The precipitate is crystallized from ethyl acetate-petroleum ether to give the title compound, mp 160°–164° C.

EXAMPLE 4 t-Butoxycarbonyl-glycyl-asparaginyl-phenylalanyl-phenylalanine Methyl Ester (Boc-Gly-Asn-Phe-Phe-OMe)

A solution of asparaginyl-phenylalanyl-phenylalanine methyl ester trifluoroacetate (0.88 g, 1.59 mmole, described by H. U. Immer et al., U.S. Pat. No. 3,917,578, issued Nov. 4, 1975), t-butoxycarbonyl-glycine trichlorophenyl ester (0.56 g, 1.59 mmole) and N-ethylmorpholine (0.203 ml, 1.59 mmole) in dimethylformamide (9 ml) is stirred at 0° C. for 1 hour and at 25° C. for 20 hours. The solution is evaporated and the residue is crystallized from methanol to give the title compound, mp 211°–214° C.

EXAMPLE 5

3-Tritylthiopropionyl-glycyl-asparaginyl-phenylalanyl-phenylalanine Methyl Ester(7; Trt-SCH$_2$CH$_2$CO-Gly-Asn-Phe-Phe-OMe)

A solution of t-butoxycarbonyl-glycyl-asparaginyl-phenylalanyl-phenylalanine methyl ester (0.525 g, 0.879 mmole, described in Example 4) in trifluoroacetic acid (10 ml) is stirred at 0° C. for 90 minutes and evaporated. The residue is dissolved in methanol (1 ml) and diethyl ether (100 ml) is added. The precipitate is collected and dried. A solution of the precipitate, N-ethylmorpholine (0.11 ml, 0.85 mmole) and 3-tritylthiopropionic acid pentachlorophenyl ester (0.556 g, 0.935 mmole) in dimethylformamide (25 ml) is stirred at 0° C. for 1 hour and at 25° C. for 20 hours and evaporated. The residue is triturated with methanol and the precipitate is dried to give the title compound as a powder, mp 234°–236.5° C.

EXAMPLE 6

3-tritylthiopropionyl-($N^6$-t-butoxycarbonyl)lysyl-glycyl-phenylalanyl-phenylalanine Hydrazide (2; Trt-SCH$_2$CH$_2$CO-Lys(Boc)-Gly-Phe-Phe-NHNH$_2$)

A solution of 3-tritylthiopropionyl-($N^6$t-butoxycarbonyl)lysyl-glycyl-phenylalanyl-phenylalanine methyl ester (0.60 g, 0.637 mmole, described in Example 3) and hydrazine hydrate (1.23 ml) in methanol (10 ml) is stirred overnight at room temperature. Water is added and the precipitate is collected. The precipitate is washed with water and dried under reduced pressure, analysis:

Calcd. for C$_{53}$H$_{63}$N$_7$O$_7$S.½H$_2$O: C,66.91%; H,6.78%; N, 10.31%.

Found: C,67.03%; H,6.87%; N,10.67%.

In the same manner but replacing 3-tritylthiopropionyl-($N^6$t-butoxycarbonyl)-lysyl-glycyl-phenylalanyl-phenylalanine methyl ester with an equivalent amount of 3-tritylthiopropionyl-glycyl-asparaginyl-phenylalanyl-phenylalanine methyl ester (described in Example 5), 3-tritylthiopropionyl-glycyl-asparaginyl-phenylalanyl-phenylalanine hydrazide, mp 240° C., is obtained.

EXAMPLE 7

3-Tritylthiopropionyl-(N⁶-t-butoxycarbonyl)lysyl-glycyl-phenylalanyl-phenylalanyl-tryptophyl-(N⁶-t-butoxycarbonyl)lysyl-(O-t-butyl)threonyl-phenylalanyl-(O-t-butyl)theonyl-(O-t-butyl)serine 2-(tritylthio)ethylamide (4; Trt-SCH$_2$CH$_2$CO-Lys(Boc)-Gly-Phe-Phe-Trp-Lys(Boc)-Thr(bu$^t$)-Phe-Thr(Bu$^t$)-Ser(Bu$^t$)-NH-CH$_2$CH$_2$S-Trt)

A solution of hydrogen chloride in ethyl acetate (1.93 M, 0.63 ml) is added to a solution at −20° C. of 3-tritylthiopropionyl-(N⁶-t-butoxycarbonyl)-lysyl-glycyl-phenylalanyl-phenylalanine hydrazide (0.45 g, 0.478 mmole, described in Example 6) in dimethylformamide (10 ml). t-Butylnitrite (0.063 ml, 0.575 mmole) is added and the solution is stirred at −15° C. for 15 minutes. A solution at −15° C. of tryptophyl-(N⁶-t-butoxycarbonyl)lysyl-(O-t-butyl)-threonyl-phenylalanyl-(O-t-butyl)-threonyl-(O-t-butyl)serine 2-(tritylthio)ethylamide (0.70 g, 0.505 mmole, described in U.S. Pat. No. 3,917,581)and N-ethyl diisopropylamine (0.288 ml, 1.6 mmole) in dimethylformamide (10 ml) is added slowly. The reaction solution is stirred at −15° C. for 1 hour and at 25° C. overnight and evaporated. The residue is triturated with water, dried and dissolved in chloroform. Diethyl ether is added and the precipitate is collected, washed with methanol and dried to give the title compound as a powder, amino acid analysis: Gly(1.00), Lys(1.95), Thr(1.77) and Phe(3.00).

In the same manner but replacing 3-tritylthiopropionyl-(N⁶-t-butoxycarbonyl)lysyl-glycyl-phenylalanyl-phenylalanine hydrazide with an equivalent amount of 3-tritylthiopropionyl-glycyl-asparaginyl-phenylalanyl-phenylalanine hydrazide (described in Example 6), 3-tritylthiopropionyl-glycyl-asparaginyl-phenylalanyl-phenylalanyl-tryptophyl-(N⁶-t-butoxycarbonyl)lysyl-(O-t-butyl)threonyl-phenylalanyl-(O-t-butyl)threonyl-(O-t-butyl)seryl-2-trityl-thioethylamide, amino acid analysis: Gly(1.00), Asp(0.89), Thr(1.98), Phe(3.00) and Lys(1.08), is obtained.

EXAMPLE 8

Cyclic Disulfide of 3-mercaptopropionyl-lysyl-glycyl-phenylalanyl-phenylalanyl-tryptophyl-lysyl-threonyl-phenylalanyl-threonyl-seryl-2-mercaptoethylamide A solution of 3-tritylthiopropionyl-(N⁶-t-butoxycarbonyl)lysyl-glycyl-phenylalanyl-phenylalanyl-tryptophyl-(N⁶-t-butoxycarbonyl)lysyl(O-t-butyl)-threonyl-phenylalanyl-(O-t-butyl)threonyl-(O-t-butyl)serine 2-(tritylthio)ethylamide (0.560 g, 0.25 mmole, described in Example 7) in a mixture of chloroform (200 ml) and methanol (20 ml) is added dropwise to a stirring solution of iodine in methanol (0.5%, 127 ml). The solution is stirred at 25° C. for 1 hour and cooled to 0° C. Aqueous sodium thiosulfate solution (1N) is added dropwise until a colorless solution is obtained. The solution is evaporated and the residue is triturated with water. The precipitate is collected and dried to give a powder of the cyclic disulfide of 3-mercaptopropionyl(N⁶-t-butoxycarbonyl)-lysyl-glycyl-phenylalanyl-phenylalanyl-tryptophyl-(N⁶-t-butoxycarbonyl)lysyl-(O-t-butyl)-threonyl-phenylalanyl-(O-t-butyl)threonyl-(O-t-butyl)seryl-2-mercaptoethylamide. A solution of the latter compound in concentrated hydrochloric acid (19 ml) is stirred rapidly at 0° C. for 10 minutes under an atmosphere of nitrogen. Acetic acid (180 ml) is added and the solution is lyophilized. The residue is dissolved in 0.2M aqueous ammonium acetate and the solution is passed through a column of carboxymethyl cellulose using 0.2M aqueous ammonium acetate. The appropriate eluate fractions are lyophilized and the residue is dissolved in the upper phase of the solvent system butanol-acetic acid-water (4:1:5), applied to a column of a chemically modified cross-linked dextran (sephadex G-25, prepared in the lower phase of the above solvent system and then equilibrated in the upper phase of the above solvent system) and the column is eluted with the upper phase solvent. The eluates are evaporated, the residue is dissolved in 5% acetic acid and lyophilized to give the title compound as the acetate salt; ir(methanol) 290 (ε=4,955) and 282 nm (ε=5,545). The latter acetate salt of the title compound is lyophilized from water to give the title compound, amino acid analysis: Gly(1.00), Lys(1.95), Thr(1.73), Ser(0.75) and Phe(2.92).

In the same manner but replacing 3-tritylthiopropionyl-(N⁶-t-butoxycarbonyl)lysyl-glycyl-phenylalanyl-phenylalanyl-tryptophyl-(N⁶-t-butoxycarbonyl)lysyl-(O-t-butyl)threonyl-phenylalanyl-(O-t-butyl)threonyl-(O-t-butyl)seryl-2-tritylthioethylamide with an equivalent amount of 3-tritylthiopropionyl-glycyl-asparaginyl-phenylalanyl-phenylalanyl-tryptophyl-(N⁶-t-butoxycarbonyl)lysysl-(O-t-butyl)threonyl-phenylalanyl-(O-t-butyl)threonyl-(O-t-butyl)seryl-2-tritylthioethylamide, the cyclic disulfide of 3-mercaptopropionyl-glycyl-asparaginyl-phenylalanyl-phenylalanyl-tryptophyl-lysyl-threonyl-phenylalanyl-threonyl-seryl-2-mercaptoethylamide (1; A=Gly-Asn), amino acid analysis: Gly(1.00), Lys(1.16), Asp(0.97), Thr(1.88), Scr(0.80) and Phe(3.05), is obtained.

We claim:

1. A compound of the formula 1

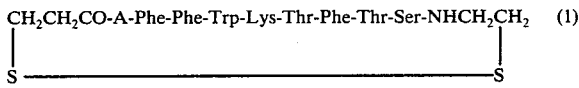

(1; A=Lys-Gly)

in which A is Gly-Asn or a therapeutically acceptable salt thereof.

2. A compound of the formula 1a

HSCH$_2$CH$_2$C0-A-Phe-Phe-Trp-Lys-Thr-Phe-Thr-Ser-NHCH$_2$CH$_2$SH  (1a)

in which A is Gly-Asn or a therapeutically acceptable salt thereof.

3. A compound of the formula 5

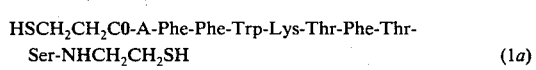

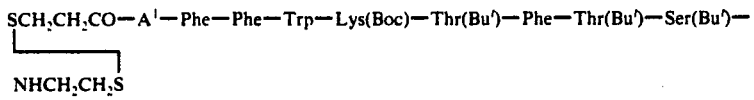

in which $A^1$ is Gly-Asn.

4. A compound of the formula 4

Trt-SCH$_2$CH$_2$CO-A$^1$-Phe-Phe-Trp-Lys(Boc)-Thr(Bu$^t$)-Phe-Thr(Bu$^t$)-Ser(Bu$^t$)-NHCH$_2$CH$_2$S-Trt in which $A^1$ is Gly-Asn.

5. A compound of the formula 2

Trt-SCH$_2$CH$_2$CO-A$^1$-Phe-Phe-NHNH$_2$   (2)

in which $A^1$ is Gly-Asn.

6. A compound of the formula 7

Trt-SCH$_2$CH$_2$CO-A$^1$-Phe-Phe-OMe   (7)

which $A^1$ is Gly-Asn.

7. A pharmaceutical composition which comprises a compound of the formula 1 or a therapeutically acceptable salt thereof, as claimed in claim 1, and a pharmaceutically acceptable liquid or solid carrier therefor.

8. A method of treating acromegaly or of managing diabetes in mammals, which comprises administering to said mammal an effective dose of a compound of the formula 1 or a therapeutically acceptable salt thereof, as claimed in claim 1.

9. A pharmaceutical composition which comprises a compound of the formula 1a or a therapeutically acceptable salt thereof, as claimed in claim 2, and a pharmaceutically acceptable liquid or solid carrier therefor.

10. A method of treating acromegaly or of managing diabetes in mammals, which comprises administering to said mammal an effective dose of a compound of the formula 1a or a therapeutically acceptable salt thereof, as claimed in claim 2.

* * * * *